United States Patent [19]

Meilland

[11] Plant 4,961

[45] Dec. 7, 1982

[54] MINIATURE ROSE PLANT—MEIJIDIRO VARIETY

[75] Inventor: Marie L. Meilland, Antibes, France

[73] Assignee: The Conard-Pyle Company, West Grove, Pa.

[21] Appl. No.: 269,761

[22] Filed: Jun. 2, 1981

[30] Foreign Application Priority Data

Jun. 5, 1980 [FR] France ..... 80 2673

[51] Int. Cl.[3] ..... A01H 5/00

[52] U.S. Cl. ..... Plt./9

[58] Field of Search ..... Plt./9, 10

*Primary Examiner*—James R. Feyrer

*Attorney, Agent, or Firm*—Burns, Doane, Swecker & Mathis

[57] ABSTRACT

A new and distinct variety of rose plant of the Miniature Class is provided having double flowers which are azalea pink in color. The present variety is a bud mutation of the Meijikatar Variety (U.S. Plant Pat. No. 4,682) which has double flowers which are brilliant vermillion red in color.

19 Drawing Figures

SUMMARY OF THE INVENTION

The new variety resulted from the study of many miniature rose plants formed by the budding of the Meijikatar variety (U.S. Plant Pat. No. 4,682) at Cap d'Antibes, Alpes Maritimes, France. As indicated in U.S. Plant Pat. No. 4,682, the Meijikatar variety exhibits brilliant vermillion red double flowers.

The present variety is a bud mutation of the Meijikatar variety which was discovered as a result of my study having attractive azalea pink double flowers. In all other respects my new variety possesses characteristics which substantially correspond to those of the Meijikatar variety.

In view of these characteristics the new variety meets the needs of the horticultural industry for all purposes, and particularly is suited for landscaping.

Extensive testing has confirmed the behavior and characteristics of the new variety. Such testing has been carried out both inside and outside greenhouses employing a variety of temperature conditions and understocks. A miniature plant was produced in all instances having attractive azalea pink double flowers of long duration which were formed in abundance.

The characteristics and properties of the new variety obtained as indicated above are strictly transmissible by asexual propagation, e.g., by budding. The rose plant of the new variety has been designated the Meijidiro variety.

BRIEF DESCRIPTION OF THE PHOTOGRAPH

The accompanying photograph shows as nearly true as it is reasonably possible to make the same in a color illustration of this character, typical specimens of plant parts of the new variety cultivated in greenhouses at the Cap d'Antibes, Alpes Maritimes, France, illustrated in:

FIG. 1—a specimen of a young shoot;

FIG. 2—a specimen of a young shoot with buds before the opening of the sepals;

FIG. 3—a specimen of a bud as the sepals begin to open;

FIG. 4—a specimen of the bud as the petals begin to open;

FIG. 5—a specimen of the flower in course of opening;

FIG. 6—a specimen of the fully opened flower—plan view—obverse;

FIG. 7—a specimen of the fully opened flower—plan view—reverse;

FIG. 8—a specimen of the flower at the end of the blooming stage—plan view—obverse;

FIG. 9—a specimen of the flower at the end of the blooming stage—plan view—reverse;

FIG. 10—a specimen of a petal—obverse;

FIG. 11—a specimen of a petal—reverse;

FIG. 12—a specimen of the receptacle showing the arrangement of the stamens;

FIG. 13—a specimen of the receptacle showing the arrangement of the pistils (stamens removed);

FIG. 14—a specimen of a main branch;

FIG. 15—a specimen of a young flowering stem;

FIG. 16—a specimen of a more mature flowering stem;

FIG. 17—a specimen of a leaf with three leaflets—upper surface;

FIG. 18—a specimen of a leaf with five leaflets—under surface; and

FIG. 19—a specimen of a leaf with seven leaflets—upper surface.

DETAILED DESCRIPTION

Figures 1, 2, 3, 4, 5, 6, 7, 8, 9, 10, 11, 12, 13, 14, 15, 16, 17, 18, 19:
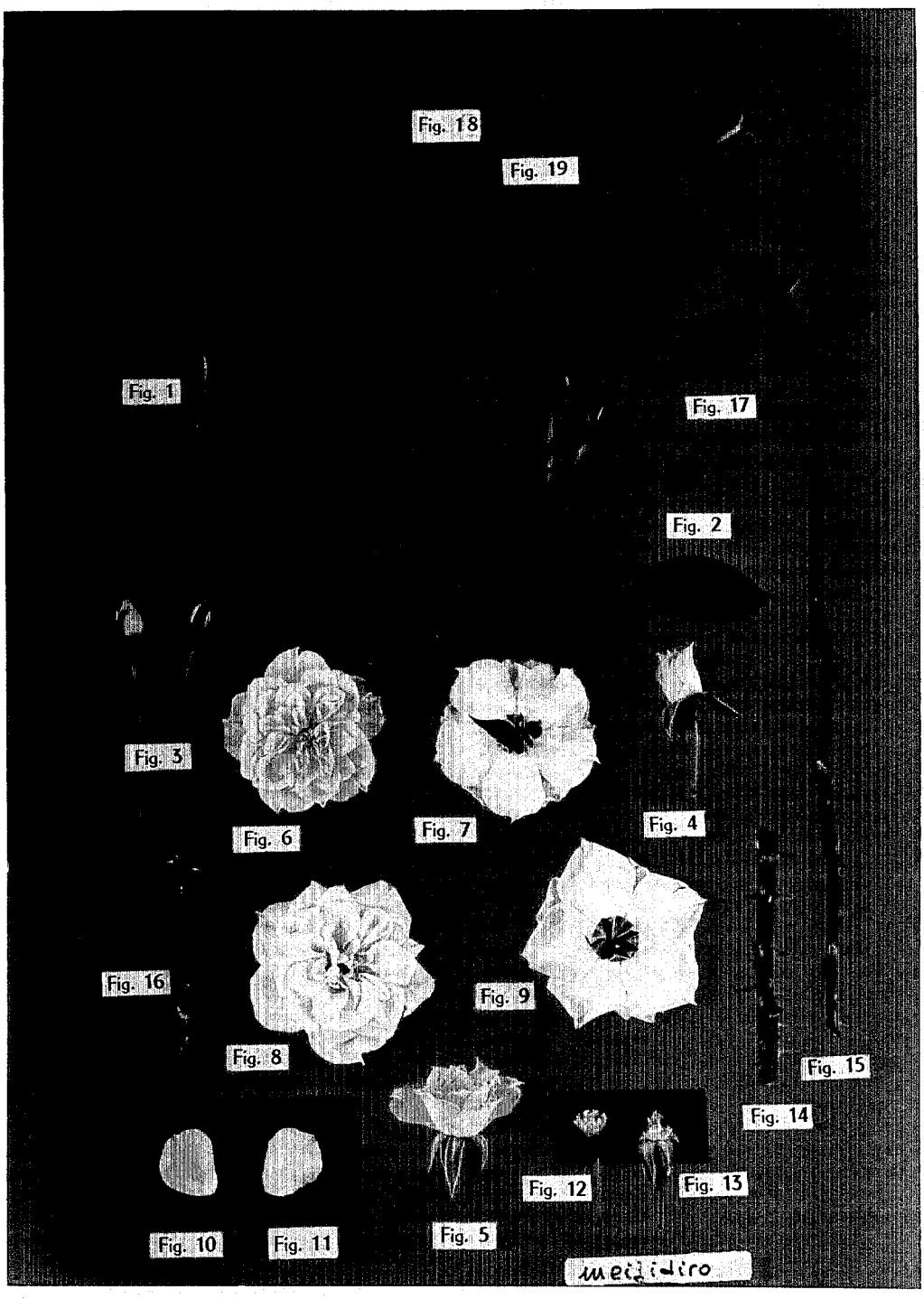

The plants described were grown in greenhouses at Cap d'Antibes, Alpes Maritimes, France.

The chart used in the identification of the colors is that of The Royal Horticultural Society (R.H.S. Colour Chart). The terminology preceding the numbered references has been added to designate in common terms, the corresponding colors.

Class: Miniature.

Plant:

*Height.*—30 cm. on average.

*Habit.*—Bushy.

Branches:

*Color.*—Young stems: Light green 144A (yellow-green group), with somewhat reddish shading. Mature wood: Bronzed green 146A (yellow-green group).

*Thorns.*—Shape: Upper edge: Straight, very thin. Under edge: Slightly concave. Size: Medium. Quantity: Fairly numerous. Color: On young stems: Reddish. On mature wood: Straw, then becoming havana brown.

Leaves:

*Stipules.*—Adnate, pectinate, rather narrow and linear.

*Petioles.*—Inner surface: Grooved, reddish brown (young foliage); medium green (adult foliage — edges more or less glandular). Outer surface: Reddish (young foliage); light green (adult foliage). This side carries a few hooked thorns.

*Leaflets.*—Number: 3-5-7 (most frequently). Shape: Elliptic — slightly lanceolate. Serration: Simple and regular. Texture: Leathery. General effect: Small, dense and dull colored. Color: Young foliage: Upper surface: Dark green 147A (yellow-green group). Under surface: Medium green 147B (yellow-green group). Adult foliage: Upper surface: Bronzed green 146A (yellow-green group). Under surface: Light green 147C (yellow-green group).

Inflorescence:

*Number of flowers.*—1 to 3 flowers per stem.

*Peduncle.*—Straight, rigid, slightly spotted with reddish brown. It is slightly glandular and bears a few hooked thorns. It is sometimes very lightly grooved. Length: 2.3 cm. on average.

*Sepals.*—Upper surface: Tomentous, greenish, exhibiting somewhat reddish spots. Under surface: Light green, exhibiting to some extent reddish spots and more or less glandular. The outside sepals have slightly appendiculate edges.

*Buds.*—Shape: Conical at the time of the opening of the sepals. Length: 1.1 cm. on average, not counting the calyx, at the opening of the sepals. Size: Small.

*Flower.*—Form: Double. Shape: At first a hollow cup, then flattened cup, stamens showing. Diameter: 4.8 cm. on average. Color: Azalea pink 35D (orange-red group). Fragrance: Very light. Lasting quality: Very long. Corolla: Petals: Texture: Consistent. Form: Round, slightly flattened with a small point at the top. The petals become cuneiform at the center and tend to fold along a median line. The unguis is small and whitish on both faces. Number: 40 on average, as well as approximately 15 petals which are not completely formed at the center of the bloom. The petals fall cleanly after the normal life of the bloom has ended. Stamens: Number: 49 on average. Anthers: Normal, yellow. Filaments: Yellow base, very lightly tinted with fuschia top. Pistils: Number: 36 on average. Stigmas: Normal, yellowish. Styles: Free, straw with fuschia top, more or less twisted and tomentous; irregular heights. Receptacle: Light green, more or less spotted with reddish brown; at the dehiscence of the anthers and in longitudinal cross-section it is very narrow and funnel shaped.

Development:

*Vegetation.*—Vigorous.

*Blossoming.*—Abundant.

*Fruiting ability.*—Very low.

*Resistance to diseases.*—Good.

I claim:

1. A new and distinct variety of miniature rose plant which originated as a bud mutation of the Meijikatar variety, substantially as shown and described, having azalea pink double flowers instead of the vermillion red double flowers exhibited by the Meijikatar variety.

* * * * * meijidiro